(12) United States Patent
Foley et al.

(10) Patent No.: US 7,434,325 B2
(45) Date of Patent: Oct. 14, 2008

(54) SYSTEMS AND METHODS FOR DETERMINING OPTIMAL RETRACTOR LENGTH IN MINIMALLY INVASIVE PROCEDURES

(75) Inventors: Kevin T. Foley, Germantown, TN (US); Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 870 days.

(21) Appl. No.: 10/899,225

(22) Filed: Jul. 26, 2004

(65) Prior Publication Data
US 2006/0020284 A1 Jan. 26, 2006

(51) Int. Cl.
*A61B 5/107* (2006.01)
*A61B 1/313* (2006.01)
*G01B 5/18* (2006.01)

(52) U.S. Cl. .......................................... 33/512; 33/836
(58) Field of Classification Search ................... 33/512, 33/832, 833, 836; 600/587
See application file for complete search history.

(56) References Cited

U.S. PATENT DOCUMENTS

| | | | |
|---|---|---|---|
| 2,235,979 A | 3/1941 | Brown | |
| 3,941,127 A | 3/1976 | Froning | |
| 3,964,480 A | 6/1976 | Froning | |
| 4,545,374 A | 10/1985 | Jacobson | |
| 4,573,448 A | 3/1986 | Kambin | |
| 4,760,847 A | 8/1988 | Vaillancourt | |
| 4,899,729 A | 2/1990 | Gill | |
| 5,158,543 A | 10/1992 | Lazarus | |
| 5,158,545 A | 10/1992 | Trudell et al. | |
| 5,292,309 A | 3/1994 | Van Tassel et al. | |
| 5,312,374 A | 5/1994 | Gurmarnik | |
| 5,370,625 A | 12/1994 | Shichman | |
| 5,389,080 A | 2/1995 | Yoon | |
| 5,395,317 A | 3/1995 | Kambin | |
| 5,396,880 A | 3/1995 | Kagan | |
| 5,403,264 A | 4/1995 | Wohlers et al. | |
| 5,439,464 A | 8/1995 | Shapiro | |
| 5,472,426 A | 12/1995 | Bonati et al. | |
| 6,027,518 A | 2/2000 | Gaber | |

(Continued)

FOREIGN PATENT DOCUMENTS

CA 2476208 8/2003

(Continued)

OTHER PUBLICATIONS

METRx™ Microdiscectomy Surgical Technique; Medtronic Sofamor Danek; as described by Donald L. Hilton, Jr., M.D., F.A.C.S.; Sylvain Palmer, M.D., F.A.C.S.; 2001.

(Continued)

*Primary Examiner*—G. Bradley Bennett
(74) *Attorney, Agent, or Firm*—Krieg DeVault LLP

(57) ABSTRACT

A measurement instrument is provided with indicia extending therealong. The measurement instrument indicia is correlated with an indicator of a reference instrument. The measurement instrument is positionable adjacent the entry location of a portal into a patient when the reference instrument is in the portal. The indicator of the reference instrument is correlated to a target location in the patient, and a location of the indicator along the indicia provides an indication of the optimal length for a retractor to be positioned in the portal.

38 Claims, 2 Drawing Sheets

U.S. PATENT DOCUMENTS

| | | |
|---|---|---|
| 6,159,179 A | 12/2000 | Simonson |
| 6,200,274 B1 | 3/2001 | McNeirney |
| 6,450,976 B2 * | 9/2002 | Korotko et al. ............. 600/587 |
| 6,679,833 B2 | 1/2004 | Smith et al. |
| 6,764,453 B2 * | 7/2004 | Meier .......................... 600/587 |
| 7,172,599 B2 * | 2/2007 | Steffensmeier et al. ....... 33/512 |
| 2003/0083688 A1 | 5/2003 | Simonson |
| 2003/0187431 A1 | 10/2003 | Simonson |
| 2005/0066535 A1 * | 3/2005 | Rupp et al. ................... 33/512 |
| 2006/0064038 A1 * | 3/2006 | Omata et al. ................ 600/587 |
| 2007/0088366 A1 * | 4/2007 | Fernanadez ................. 600/587 |
| 2007/0151116 A1 * | 7/2007 | Malandain ................... 33/512 |
| 2007/0173745 A1 * | 7/2007 | Diederich et al. ........... 600/587 |

FOREIGN PATENT DOCUMENTS

| | | |
|---|---|---|
| FR | 2 714 285 | 6/1995 |
| WO | WO 03/065910 A1 | 8/2003 |
| WO | WO 2004/071288 A1 | 8/2004 |

OTHER PUBLICATIONS

Micro-Endo™ Systems Brochure; Sofamor Danek; 1994.

* cited by examiner

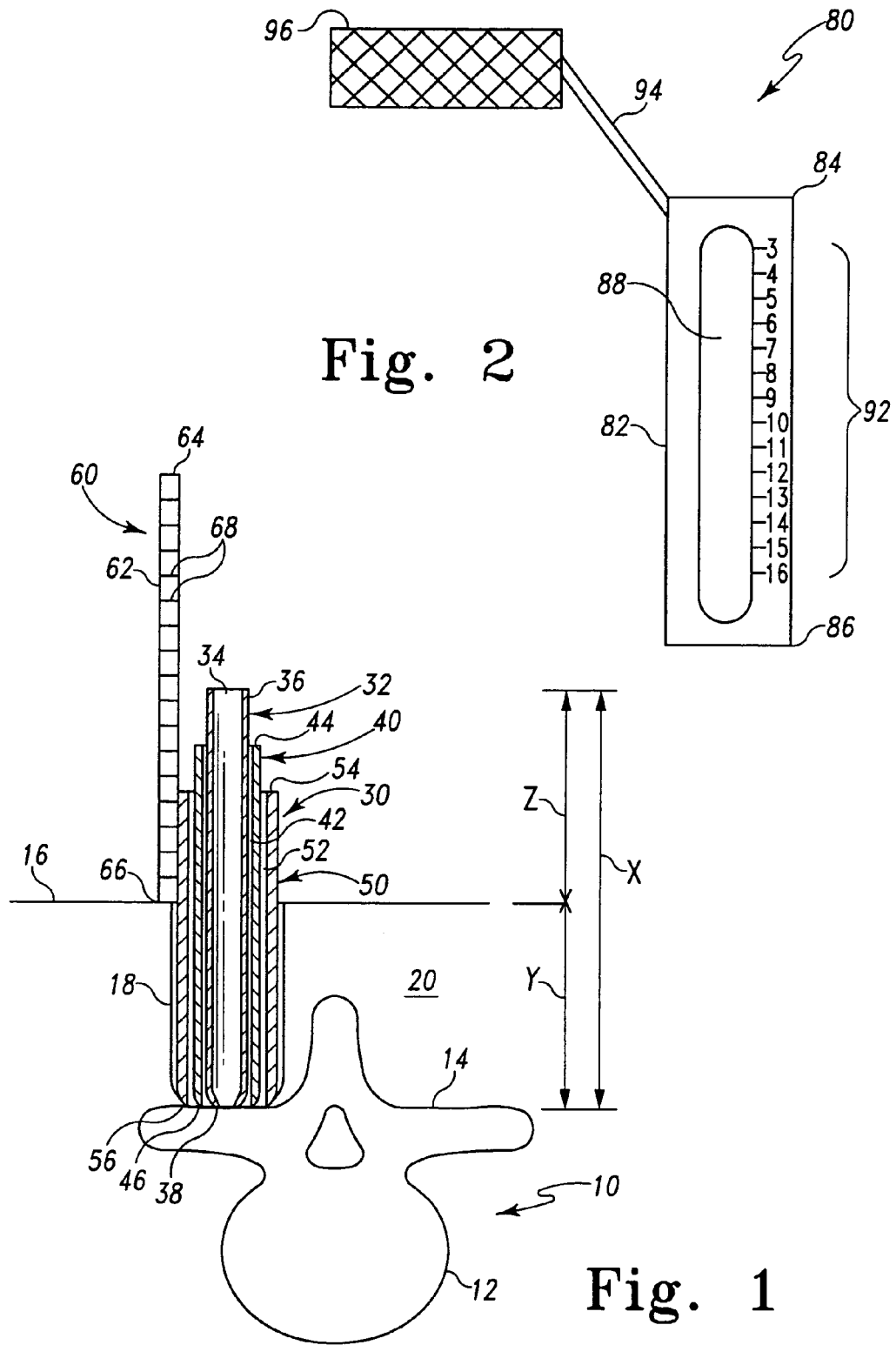

SYSTEMS AND METHODS FOR DETERMINING OPTIMAL RETRACTOR LENGTH IN MINIMALLY INVASIVE PROCEDURES

BACKGROUND

Minimally invasive instruments and methods for accessing the spinal column minimize tissue retraction and dissection in order to promote healing and faster recovery times. One or more retractors can be positioned in an access portal to facilitate access to locations deep within the body while maintaining the minimally invasive character of the procedure. The smaller access portals can increase the difficulty in determining the optimal length for the retractor since measurement devices placed in or through the portal include indicia or markings obscured by the skin or tissue below the incision or by other instruments positioned in the access portal. Systems and methods which improve the ability to measure and determine optimal retractor length for positioning in minimally invasive access portals are desirable.

SUMMARY

According to one aspect, a system for determining an optimal length for a retractor for use in a minimally invasive procedure with a patient is provided. The system includes a reference instrument with a predetermined length between its distal end and an indicator thereon. The distal end is positionable in a portal to a target location in the patient with the indicator located proximally of an entry location of the portal. The system also includes a measurement instrument including indicia extending therealong. In use, the reference instrument is positionable in the portal with its distal end adjacent the target location and the measurement instrument is positionable along the reference instrument with its distal end adjacent the entry location outside the portal. A location of the indicator of the reference instrument along the indicia of the measurement instrument provides an indication of the optimal length of the retractor for positioning in the portal.

According to another aspect, a system for determining an optimal length for a retractor for use in a minimally invasive procedure with a patient is provided. The system includes at least one tissue dilator including a predetermined length between a distal end and an indicator thereon. The distal end is positionable in a portal to a target location in the patient with the indicator located proximally of an entry location of the portal. The system further includes a measurement instrument including indicia extending therealong. When the measurement instrument is along the at least one tissue dilator in the portal with the dilator distal end adjacent the target location and the distal end of the measurement instrument adjacent the entry location, a location of the indicator along the indicia provides an indication of the optimal length of the retractor for positioning in the portal.

According to a further aspect, a measurement instrument for determining an optimal retractor length for use with a minimally invasive procedure in a patient is provided. The measurement instrument includes a body extending between a distal end and a proximal end. The body includes indicia extending therealong between the distal and proximal ends. The indicia includes a scale increasing in value from the proximal end to the distal end. In use, the distal end is positionable adjacent an entry location of the patient with the body along an indicator correlated to a target location in the patient. A location of the indicator along the indicia provides an indication of the optimal retractor length.

According to a further aspect, a method for determining an optimal retractor length for a minimally invasive access portal in a patient is provided. The method includes inserting a reference instrument in the portal, the reference instrument including an indicator located proximally of an entry location of the portal when a distal end of the reference instrument is adjacent a target location in the patient; positioning a distal end of a measurement instrument adjacent the entry location, the measurement instrument including indicia extending therealong proximally of the entry location; and observing a location of the indicator along the indicia to determine the optimal retractor length.

These and other aspects will also be apparent from the following description.

BRIEF DESCRIPTION OF THE FIGURES

FIG. 1 is a section view of one embodiment system in partial section for determining optimal retractor length in a minimally invasive procedure.

FIG. 2 is an elevation view of another embodiment instrument for use with a system and method for determining optimal retractor length in a minimally invasive procedure.

DESCRIPTION OF THE ILLUSTRATED EMBODIMENTS

Figure 3:
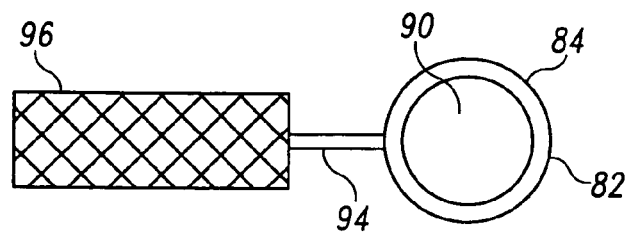
FIG. 3 in an end view of the instrument of FIG. 2.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

A measurement instrument is provided that is positionable adjacent to and outside of an access portal and along an indicator correlated to a target location in the patient. The measurement instrument includes indicia extending thereal-ong, and a location of the indicator relative to the indicia provides an indication of the optimal length of a retractor for positioning in the patient to the target location.

In one embodiment, the measurement instrument is a dilator positionable in the patient to guide placement of one or more additional dilators thereover. The measurement instrument dilator is removable after the placement of the one or more additional dilators thereover. The measurement instrument dilator includes indicia and is positionable adjacent to and outside the entry location in the patient along the one or more dilators in the patient. At least one of the other dilators includes an indicator positioned along the indicia to provide an indication of the optimal length of the retractor to be positioned in the patient.

In another embodiment, the measurement instrument is a tube positionable over one or more indicators correlated to the target location. A location of the indicator relative to indicia along the tube provides an indication of the optimal retractor length. In one form, the tube includes a window extending therealong and indicia extending along the window. In a further form, the tube includes a handle extending therefrom to facilitate handling and manipulation of the measurement instrument.

The indicator can be provided with any instrument correlated to the target location in the patient to provide an indication of optimal retractor length when the measurement instrument is positioned adjacent thereto. In one embodiment, the indicator is the proximal end of a dilator positionable in the incision with a distal end adjacent the target location in the patient. Other embodiments contemplate that the indicator can be a mark, structure, or other signal on any instrument positionable in the patient with the distal end adjacent the target location and the indicator located outside the patient.

The optimal length of the retractor can correspond to any length providing a desired positioning of a distal end of the retractor adjacent a target location in the body and a proximal end of the retractor adjacent an entry location into the patient. The length can be sized to position the proximal end at the entry location, to space the proximal end proximally of the entry location, or to recess the proximal end in the patient distally of the entry location. Examples of suitable retractors are provided in U.S. Pat. No. 6,679,833, which is incorporated herein by reference in its entirety. In one form, the length of the retractor from the target location positions the proximal end of the retractor at the entry location into the patient to provide a protected passageway through the skin and/or tissue while minimizing the extent of the retractor from the entry location. In another form, the length of the retractor from the target location positions the proximal end of the retractor such that it extends proximally from the entry location to facilitate attachment of auxiliary instruments to the proximal end, such as an endoscope.

The retractor can be in the form of a tube, sleeve or cannula to provide a protected passageway in the patient to the target location. The retractor can be expandable, rigid, flexible, and combinations of rigid and expandable portions. The retractor can be comprised of one or more blades that extend completely about the portal, or that expose tissue along the portal. When positioned in the portal, the distal end of the retractor is located adjacent the target location, and the retractor can be movable in the incision to reposition the distal end, or the retractor can be fixed to bony tissue. The retractor can be employed with any one or combination of viewing systems for viewing the target location through the incision, or through a portal adjacent the incision. Such viewing systems include fluoroscopic systems, X-ray systems, CT imaging, endoscopes, microscopes, loupes, and naked eye visualization, for example.

Referring to FIG. 1, there is shown a vertebra 10 having an anterior vertebral body portion 12 and posterior elements 14. Portal 18 can be formed through the skin 16 and tissue 20 to provide minimally invasive access to a target location relating to the spinal column. Portal 18 can be dilated through skin 16 and/or tissue 20 to access the posterior vertebral elements through a dilated minimally invasive access portal. The entry location into the patient can be at skin 16 or at some location along tissue 20. Furthermore, portal 18 can be created by an incision, puncture, or combination thereof in skin 16 and/or tissue 20.

A dilator system 30 is positionable in portal 18 and extends through skin 16 and tissue 20 to orient the distal end of dilator system 30 adjacent the target location, such as near the posterior vertebral elements 14 as shown. The target location can include any one or combination of anterior vertebral body portion 12, posterior elements 14, a disc space between vertebrae, the facets, laminae, pedicles, transverse processes, spinous processes, the foramen, or any other bone or tissue structure adjacent or in the spinal column.

Dilator system 30 can include any number of dilators, ranging from one dilator to three or more dilators. In FIG. 1, three dilators are shown. An inner dilator 32 extends between a proximal end 36 and a distal end 38. Inner dilator 32 includes a central bore 34 extending between and opening at proximal and distal ends 36, 38. Other embodiments contemplate an inner dilator 32 that is solid.

An intermediate dilator 40 extends between a proximal end 44 and a distal end 46. Intermediate dilator 40 includes a central bore 42 extending between and opening at proximal and distal ends 44, 46. Intermediate dilator 40 includes a length between proximal and distal ends 44, 46 that is less than the length of inner dilator 32 between proximal and distal ends 36, 38. Accordingly, when distal ends 38, 46 are aligned adjacent one another as shown, proximal end 36 extends proximally further than proximal end 44. Other embodiments contemplate that more than one intermediate dilator is provided, with the proximal ends of the inner ones of the intermediate dilators extending proximally further than the proximal end of the adjacent, outer intermediate dilator when the distal ends are aligned.

An outer dilator 50 extends between a proximal end 54 and a distal end 56. Outer dilator 50 includes a central bore 52 extending between and opening at proximal and distal ends 54, 56. Outer dilator 50 includes a length between proximal and distal ends 54, 56 that is less than the length of the adjacent intermediate dilator 40 between proximal and distal ends 44, 46. Accordingly, when distal ends 46, 56 are aligned adjacent one another as shown, proximal end 44 extends proximally further than proximal end 54.

Prior to inserting dilator system 30, it is contemplated that a needle can be inserted through skin 16 and/or tissue 20, and the distal end of the needle engaged to bone or other tissue adjacent the target location. The needle can include an inner bore housing a removable stylet. When the needle is engaged to the bone or other tissue, the stylet is removed and a guidewire is inserted through the inner bore of the needle for engagement with the tissue or bone engaged by the needle. The needle is then withdrawn from over the guidewire, and the guidewire remains in place to guide placement of at least the inner dilator 32. Portal 18 can be formed based on the location of the guidewire extending through skin 16 and tissue 20 of the patient prior to placement of the inner dilator 32. An incision can be made to facilitate formation of portal 18, although such is not required.

Other procedures contemplate that a needle is not employed, and that the inner dilator is positioned over the guidewire after the guidewire is guided and targeted percutaneously to the target location. In another embodiment, neither a needle nor a guidewire is employed, and a trocar or the inner dilator is guided into the patient to the target location. In any procedure, appropriate visualization systems may be employed to guide placement of the needle, guidewire, trocar and/or inner dilator, including any one or combination of an image guided navigation system, fluoroscopy, X-ray, CT imaging, microscope, endoscope, loupes, and naked eye visualization, for example.

With one or more of the dilators 32, 40, 50 positioned in portal 18 and the respective distal end 38, 46, 56 adjacent the target location, any one or combination of the dilators 32, 40, 50 can function as a reference instrument with an indicator. Furthermore, it is contemplated that a reference instrument that is not one of the dilators 32, 40, 50 can be employed, so long as it includes an indicator correlated to the targeted location in the body.

Measurement instrument 60 is positionable outside portal 18 adjacent the one or more dilators 32, 40, 50 or other instrument functioning as a reference instrument in order to determine an optimal retractor length for positioning in the portal to the target location. Measurement instrument 60 includes a body 62 extending between a proximal end 64 and a distal end 66. Indicia 68 is provided along body 62. Indicia 68 can be formed by a series of spaced markings and can include measurement numerals along each or any interval of the markings comprising indicia 68. The markings can be scaled to provide an indication of optimal retractor length for positioning in the portal.

Distal end 66 is positionable against adjacent the entry location to portal 18 along the one or more dilators 32, 40, 50. At least one of the dilators 32, 40, 50 is a reference instrument, and includes an indicator that is compared with indicia 68 to provide an indication of the optimal length for a retractor to be positioned in the portal 18. For example, in the illustrated embodiment, dilator 32 functions as a reference instrument with a known length between proximal end 36 and distal end 38. Proximal end 36 is an indicator, and its alignment along indicia 68 of measurement instrument 60 provides an indication of the optimal length of a retractor for positioning in portal 18.

In one specific embodiment, provided for purposes of illustration and not limitation, the reference instrument is dilator 32. Dilator 32 can be provided in any length from its distal end 38 to its indicator, which in the illustrated embodiment is proximal end 36. This overall length between the distal end 38 to the indicator proximal end 36 is designated with variable X. A first portion of the length X is positioned in portal 18 and extends distally of the entry location, and this first portion is designated with the variable Y. A second portion of the length X extends proximally of the entry location to portal 18, and this second portion is designated with the variable Z. Indicia 68 along measurement instrument 60 includes a scale having measurement numerals therealong that correspond to length X minus length Z. Therefore, the measurement numerals of the indicia provide a reading of the optimal length Y based on the location of proximal end 36 (the indicator) along indicia 68 of measurement instrument 60. In the illustrated embodiment, the optimal length Y is the difference in the overall length X of dilator 32 (the reference instrument) and the length Z of dilator 32 that extends proximally of the entry location to portal 18 to proximal end 36 (the indicator.)

In the illustrated embodiment of FIG. 1, the indicator corresponds to the proximal end 36 of dilator 32. It should be understood, however, that the indicator can be any mark, structure or other mechanical or electronic signal located proximally of the entry location to portal 18 and along the dilators or any other reference instrument that may be employed. Furthermore, any of the dilators 32, 40, 50 can function as the reference instrument, provided indicia 68 is calibrated to the length of the reference instrument between its distal end and its indicator. In still a further form, a number of measurement instruments 60 can be provided, each including an indicia 68 corresponding to a respective ones of the dilators 32, 40, 50 and/or other reference instrument. The surgeon can select the measurement instrument from the kit corresponding to the reference instrument that remains in the portal. To facilitate selection of the appropriate measurement instrument 60, the measurement instruments can be color coded, keyed or otherwise matched with the dilators or other reference instrument to indicate the particular reference instrument from which a measurement with a particular measurement instrument is to be obtained.

The reference instrument need not be a dilator positioned in a portal to dilate skin 16 and/or tissue 20. Rather, the reference instrument can be any tube, rod, sleeve, wire or other device positionable in portal 18 with a distal end adjacent the target location in the patient and an indicator located proximally of the entry location of portal 18 when so positioned. In still another embodiment, measurement instrument 60 can also be a dilator. For example, measurement instrument 60 can be a first inserted dilator through portal 18. After placement of one or more other dilators, measurement instrument 60 is withdrawn from portal 18, and positioned adjacent the reference instrument in portal 18 with its distal end adjacent the entry location. One of the remaining dilators, or some other reference instrument, remaining in portal 18 is employed as a reference instrument. The length of the reference instrument is calibrated to the indicia along the measurement instrument so that the location of the indicator of the reference instrument along indicia 68 is noted for selection of an optimal length retractor.

Referring to FIGS. 2 and 3, there is shown another embodiment measurement instrument 80. Measurement instrument 80 includes a body 82 extending between a proximal end 84 and a distal end 86. Body 82 includes a central passage 90 extending therealong. Passage 90 opens at proximal and distal ends 84, 86, although passage 90 can be closed at proximal end 84. Measurement instrument 80 further includes a shaft 94 extending from body 82 adjacent proximal end 84, and a handle 96 spaced from body 82 at an end of shaft 94. Handle 96 is offset from body 82 to facilitate viewing about and handling of measurement instrument 80.

Measurement instrument 80 further includes indicia 92 extending along body 82. A window 98 through body 82 communicates with passage 90. Indicia 92 can be provided along window 98, and include markings therealong providing a numerical scale corresponding with a reference instrument of predetermined length, as discussed above with respect to measurement instrument 60. The numerical scale includes measurement numerals along indicia 92 to indicate the optimal retractor length. The measurement numerals increase in value from proximal end 84 toward distal end 86. Accordingly, as the Z length (FIG. 1) of the reference instrument increases, the indicator of the reference instrument will be positioned along indicia 92 toward proximal end 84, and indicia 92 will indicate a shorter optimal length Y for the retractor. Conversely, as the Z length of the reference instrument decreases, the indicator of the reference instrument will be positioned along indicia 92 toward distal end 86, and indicia 92 will indicate a longer optimal length Y for the retractor. It is also contemplated that indicia 68 of measurement instrument 60 can include a numerical scale with measurement numerals increasing in value from proximal end 64 toward distal end 66.

Figure 4:
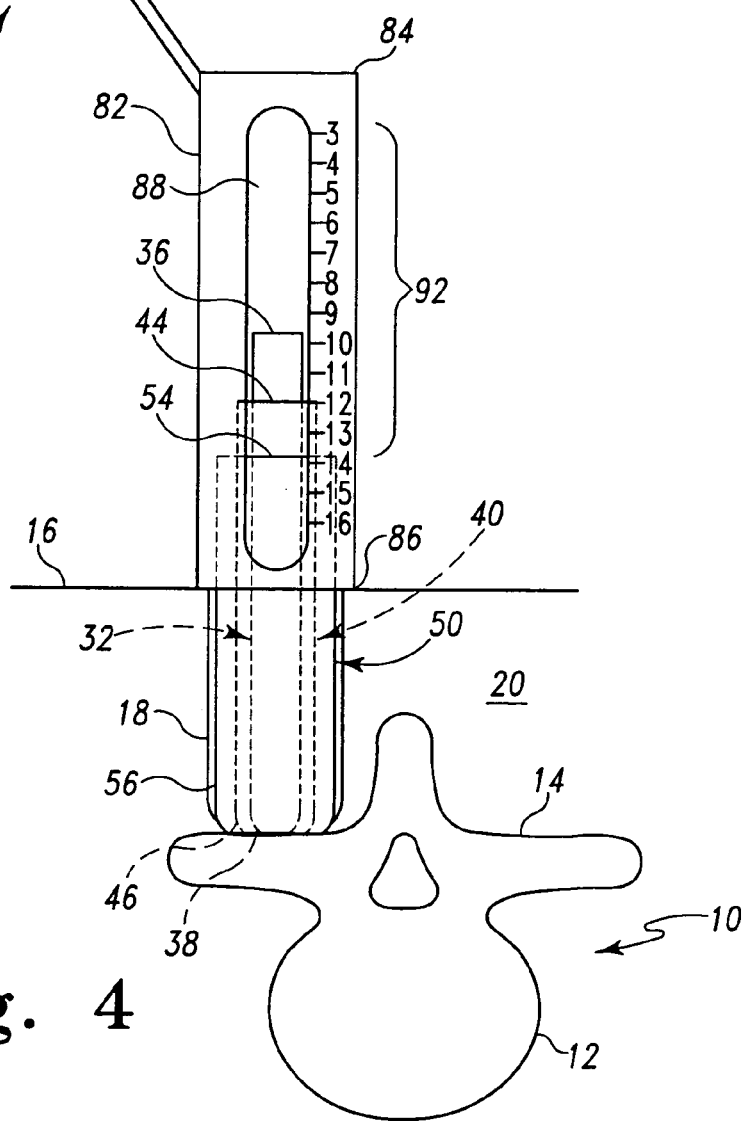
FIG. 4 is an elevation view of another embodiment system for determining optimal retractor length in a minimally invasive procedure.

As shown in FIG. 4, measurement instrument 80 is positionable about a reference instrument such as one or more dilators 32, 40, 50. The reference instrument(s) are viewable through window 88, and indicia 92 extends along window 88. The location of the indicator of the reference instrument(s), such as proximal end 36 of dilator 32, for example, along indicia 92 provides an indication of the optimal length for the retractor to be positioned in incision 18. Positioning measurement instrument 80 about the reference instrument(s) facilitates viewing of the alignment of the indicator along indicia 92. Such positioning also facilitates accurate measurement of the retractor length since distal end 86 contacts the patient about the entry location of portal 18, accounting for and averaging the effects of any variations, contours, or other conditions that might exist about the entry location to portal 18.

For each of the measurement instruments 60, 80, the measurement of the optimal retractor length is observed at a location that is spaced proximally of the entry of the reference instrument(s) into the portal. Accordingly, indicia 68, 92 are not obstructed at the measurement location by skin 16 and/or tissue 20. Thus, if the optimal retractor length falls between intervals along the indicia, it is possible to ascertain with reasonable certainty whether the optimal retractor length should correspond to the shorter or longer length indicated by the adjacent intervals of the indicia.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for determining an optimal length for a retractor for use in a minimally invasive procedure with a patient, comprising:
    a reference instrument extending between a distal end and a proximal end, said reference instrument including a predetermined length between said distal end and an indicator thereon, said distal end being positionable in a portal adjacent to a target location in the patient with said indicator located proximally of an entry location of the portal; and
    a measurement instrument extending between a distal end and a proximal end, said measurement instrument including indicia extending therealong, wherein when said reference instrument is in the portal with said distal end thereof adjacent the target location and said measurement instrument is positioned along the reference instrument with said distal end of said measurement instrument adjacent the entry location, a location of said indicator of said reference instrument along said indicia of said measurement instrument provides an indication of the optimal length of the retractor for positioning in the portal.

2. The system of claim 1, wherein said indicia includes a numerical scale increasing in value from said proximal end toward said distal end of said measurement instrument.

3. The system of claim 1, wherein said indicia provides a measurement of 0 a portion of said predetermined length of said reference instrument, said portion extending distally from the entry location to said distal end of said reference instrument when said reference instrument is positioned in the portal.

4. The system of claim 1, wherein said indicia is located on an external surface of said measurement instrument.

5. The system of claim 1, wherein said measurement instrument is a first dilator and said reference instrument is a second dilator, said second dilator being positionable about said first dilator when in said portal, said first dilator being removable with said second dilator in the portal and being positionable along the second dilator with said distal end adjacent the entry location of the portal.

6. The system of claim 1, wherein said measurement instrument includes a passage sized for positioning about at least a proximal portion of said reference instrument.

7. The system of claim 6, wherein said measurement instrument includes a window, said window extending along said measurement instrument between said distal and proximal ends of said measurement instrument.

8. The system of claim 7, wherein said indicia extends along said window.

9. The system of claim 1, wherein said reference instrument includes a number of dilators positionable one over the other to sequentially dilate tissue along the portal.

10. The system of claim 9, wherein each of said number of dilators includes a predetermined length between a distal end and an indicator thereof, and said measurement instrument is selected from a set of measurement instruments each with indicia correlated to said predetermined length of corresponding ones of said dilators.

11. The system of claim 10, wherein said selected measurement instrument includes indicia correlated to said predetermined length of a first inserted dilator.

12. The system of claim 10, wherein said selected measurement instrument includes indicia correlated to said predetermined length of a last inserted dilator.

13. The system of claim 1, wherein said indicator is said proximal end of said reference instrument.

14. A system for determining an optimal length for a retractor for use in a minimally invasive procedure with a patient, comprising:
    at least one tissue dilator extending between a distal end and a proximal end, said at least one tissue dilator including a predetermined length between said distal end and an indicator thereon, said distal end being positionable in a portal adjacent a target location in the patient with said indicator located proximally of an entry location of the portal; and
    a measurement instrument extending between a distal end and a proximal end, said measurement instrument including indicia extending therealong, wherein with said distal end of said reference instrument adjacent the target location and said measurement instrument along said at least one tissue dilator with said distal end of said measurement instrument adjacent the entry location, a location of said indicator along said indicia provides an indication of the optimal length of the retractor for positioning in the portal.

15. The system of claim 14, wherein said indicia includes a numerical scale increasing in value from said proximal end toward said distal end of said measurement instrument.

16. The system of claim 14, wherein said indicia is located on an external surface of said measurement instrument.

17. The system of claim 14, wherein said measurement instrument is a first tissue dilator and said at least one dilator includes a second tissue dilator, said second tissue dilator being positionable about said first tissue dilator in the portal, said first tissue dilator being removable with said second tissue dilator in the portal and being positionable adjacent the entry location along the second tissue dilator.

18. The system of claim 14, wherein said measurement instrument includes a passage sized for positioning about said at least one tissue dilator.

19. The system of claim 18, wherein said measurement instrument includes a window, said window extending along said measurement instrument between said distal and proximal ends of said measurement instrument.

20. The system of claim 19, wherein said indicia extends along said window.

21. The system of claim 14, wherein said at least one tissue dilator includes a number of tissue dilators positionable one over the other to sequentially dilate tissue along the portal.

22. The system of claim 21, wherein each of said number of tissue dilators includes a predetermined length between a distal end and an indicator thereof, and said measurement instrument is selected from a set of measurement instruments each with indicia correlated to said predetermined lengths of corresponding ones of said tissue dilators.

23. The system of claim 22, wherein said selected measurement instrument includes indicia correlated to said predetermined length of a first inserted dilator.

24. The system of claim 22, wherein said selected measurement instrument includes indicia corresponding to said predetermined length of a last inserted dilator.

25. The system of claim 14, wherein said indicator is said proximal end of said at least one tissue dilator.

26. The system of claim 14, wherein said indicia provides a measurement of a portion of said predetermined length of said at least one tissue dilator, said portion extending distally from the entry location to said distal end of said at least one tissue dilator when said tissue dilator is in the portal.

27. A measurement instrument for determining an optimal retractor length for use with a minimally invasive procedure in a patient, comprising:
a body extending between a distal end and a proximal end, said body including indicia extending therealong between said distal end and said proximal end, said indicia including a scale increasing in value from said proximal end to said distal end, wherein said distal end is positionable adjacent an entry location of the patient with said body along an indicator correlated to a target location in the patient, whereby a location of said indicator along said indicia provides an indication of the optimal retractor length.

28. The instrument of claim 27, wherein said body includes a passage opening at least at said distal end.

29. The instrument of claim 28, wherein said body includes a window extending therealong in communication with said passage.

30. The instrument of claim 29, wherein said indicia is adjacent said window.

31. The instrument of claim 27, further comprising a handle extending from said proximal end of said body.

32. A method for determining an optimal retractor length for a minimally invasive access portal in a patient, comprising:
inserting a reference instrument in the portal, the reference instrument including an indicator located proximally of an entry location of the portal when a distal end of the reference instrument is adjacent a target location in the patient;
positioning a distal end of a measurement instrument adjacent the entry location, the measurement instrument including indicia extending therealong proximally of the entry location; and
observing a location of the indicator along the indicia to determine the optimal retractor length.

33. The method of claim 32, wherein the indicator is a proximal end of the reference instrument.

34. The method of claim 32, further comprising:
sequentially dilating the incision with a number of dilators, wherein the measurement instrument is a first inserted dilator;
withdrawing the first inserted dilator with at least one other of the number of dilators in the portal, wherein the at least one other of the number of dilators is the reference instrument and includes the indicator; and
positioning the distal end of the measurement instrument includes positioning a distal end of the first inserted dilator adjacent the entry location along the reference instrument.

35. The method of claim 32, wherein the indicia includes a numerical scale increasing from a proximal end of the measurement instrument to a distal end of the measurement instrument.

36. The method of claim 32, wherein positioning the distal end of the measurement instrument includes positioning the measurement instrument about the reference instrument.

37. The method of claim 36, wherein observing the location of the indicator includes observing the indicator through a window of the measurement instrument.

38. The method of claim 32, wherein the indicia is correlated to a portion of a length of the reference instrument, the portion extending distally from the entry location to the distal end of the reference instrument when the reference instrument is in the portal.

* * * * *